(12) United States Patent
Volokh et al.

(10) Patent No.: US 8,835,858 B2
(45) Date of Patent: Sep. 16, 2014

(54) SYSTEMS AND METHODS FOR ATTENUATION COMPENSATION IN NUCLEAR MEDICINE IMAGING BASED ON EMISSION DATA

(75) Inventors: Lana Volokh, Haifa (IL); Yaron Hefetz, Kibbutz alonim (IL); Alexander Ganin, Whitefish Bay, WI (US); Ravindra Manjeshwar, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 235 days.

(21) Appl. No.: 13/428,840

(22) Filed: Mar. 23, 2012

(65) Prior Publication Data

US 2013/0248719 A1 Sep. 26, 2013

(51) Int. Cl.
*G01T 1/164* (2006.01)
*A61B 6/00* (2006.01)

(52) U.S. Cl.
CPC ........................................ *A61B 6/52* (2013.01)
USPC ......................................................... 250/362

(58) Field of Classification Search
CPC ........ A61B 2576/00; A61B 6/52; A61B 6/03; A61B 6/037; A61B 6/5258; G06T 7/0012; G06T 11/005; G01T 1/644
USPC ......................................................... 250/362
See application file for complete search history.

(56) References Cited

U.S. PATENT DOCUMENTS

| | | | |
|---|---|---|---|
| 5,608,221 A | 3/1997 | Bertelsen et al. | |
| 6,628,983 B1 | 9/2003 | Gagnon | |
| 7,473,900 B2 | 1/2009 | Vija | |
| 7,592,597 B2 * | 9/2009 | Hefetz et al. | 250/363.1 |
| 8,019,139 B2 * | 9/2011 | Porat et al. | 382/131 |
| 2003/0128801 A1 | 7/2003 | Eisenberg et al. | |
| 2006/0004274 A1 * | 1/2006 | Hawman | 600/407 |

FOREIGN PATENT DOCUMENTS

WO WO 2009/060351 A1 5/2009

\* cited by examiner

*Primary Examiner* — Constantine Hannaher
(74) *Attorney, Agent, or Firm* — Dean D. Small; The Small Patent Law Group

(57) ABSTRACT

Systems and methods for attenuation compensation in nuclear medicine imaging based on emission data are provided. One method includes acquiring emission data at a plurality of energy windows for a person having administered thereto a radiopharmaceutical comprising at least one radioactive isotope. The method also includes performing a preliminary reconstruction of the acquired emission data to create one or more preliminary images of a peak energy window and a scatter energy window and determining a body outline of the person from at least one of the reconstructed preliminary image of the peak energy window or of the scatter energy window. The method further includes identifying a heart contour and segmenting at least the left lung. The method additionally includes defining an attenuation map based on the body outline and segmented left lung and reconstructing an image of a region of interest of the person using an iterative joint estimation reconstruction.

26 Claims, 8 Drawing Sheets

SYSTEMS AND METHODS FOR ATTENUATION COMPENSATION IN NUCLEAR MEDICINE IMAGING BASED ON EMISSION DATA

BACKGROUND OF THE INVENTION

The subject matter disclosed herein relates generally to nuclear medicine imaging systems, and more particularly to single photon emission computed tomography (SPECT) imaging systems and compensating for emission attenuation in SPECT systems, especially in cardiac imaging, using emission data.

Different types of imaging techniques are known and used for medical diagnostic imaging. For example, diagnostic nuclear imaging, such as SPECT imaging, is used to study radionuclide distribution in a subject, such as a patient. Typically, one or more radiopharmaceuticals or radioisotopes are injected into the patient. Gamma camera detector heads, typically including a collimator, are placed adjacent to a surface of the patient to capture and record emitted radiation to thereby acquire image data. Different configurations are known wherein the gamma cameras may remain in a fixed location/orientation (e.g., focused detector modules) relative to an object of interest during a scan or may be rotated about the patient. Image reconstruction techniques, such as backprojection, may then be used to construct images of radiotracer uptake distribution within internal structures of the subject based upon the acquired image or acquired data, such as list data.

While such conventional systems may provide quality images with good diagnostic value, photon attenuation is a major physical factor affecting the quality of reconstructed images in SPECT systems. Such attenuation may occur, for example, due to tissues between the sources of emissions and the system detectors. However, in SPECT imaging, and specifically in cardiology, it is important to obtain an accurate emission image (a three-dimensional 3D map of the radioisotope distribution within the imaged patient) in the presence of attenuation (in large part due to Compton scattered radiation) caused by the patient's body.

In cardiac imaging, photon attenuation accounts for up to 85% loss of emitted photons from the myocardium area. Moreover, data inconsistencies with models used in image reconstruction from a quantitative point of view are also spatially variant (e.g., 70-85% error within myocardium only in some cases). Thus, known reconstruction methods require knowledge of the attenuation map, for example, the 3D model of the patient tissue in areas affecting the radiation arriving at the detector. These methods currently mostly rely on direction transmission measurements that may include a radioactive source that is often ineffective or measurements from an x-ray computed-tomography (CT) system that are costly, as well as can add radiation dose to the patient, additional imaging time, geometrical mis-registration and resolution differences. Models may be used to characterize the attenuation, although actual attenuation may differ substantially. Moreover, because of the high variability of patient sizes and shapes, a "patient standard" can yield a poor reconstruction result.

BRIEF DESCRIPTION OF THE INVENTION

In accordance with an embodiment, a method for image reconstruction is provided. The method includes acquiring emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window. The method also includes performing a preliminary reconstruction of the acquired emission data to create one or more preliminary images of the peak energy window and the scatter energy window and determining a body outline of the person from at least one of the reconstructed preliminary image of the peak energy window or the reconstructed preliminary image of the scatter energy window. The method further includes identifying a heart contour of the person from the reconstructed preliminary image of the peak energy window and segmenting at least the left lung of the person from the reconstructed preliminary image of the scatter energy window using the identified heart contour as a landmark. The method additionally includes defining an attenuation map based on at least the determined body outline and the segmented left lung and reconstructing an image of a region of interest of the person using an iterative joint estimation reconstruction including updating the attenuation map and the image of the peak energy window, wherein the joint estimation reconstruction comprises using data acquired in the plurality of energy windows.

In accordance with another embodiment, a nuclear medicine (NM) imaging system is provided that includes a gantry and a plurality of nuclear medicine (NM) cameras coupled to the gantry and configured to acquire emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window. The NM imaging system also includes an image reconstruction module configured to (i) perform a preliminary reconstruction of the acquired emission data to create one or more preliminary images of the peak energy window and the scatter energy window, (ii) determine a body outline of the person from at least one of the reconstructed preliminary image of the peak energy window or the reconstructed preliminary image of the scatter energy window, (iii) identify a heart contour of the person from the reconstructed preliminary image of the peak energy window, (iv) segment at least the left lung of the person from the reconstructed preliminary image of the scatter energy window using the identified heart contour as a landmark, (v) define an attenuation map based on at least the determined body outline and the segmented left lung and (vi) reconstruct an image of a region of interest of the person using an iterative joint estimation reconstruction including updating the attenuation map and the image of the peak energy window, wherein the joint estimation reconstruction comprises using data acquired in the plurality of energy windows.

In accordance with yet another embodiment, a non-transitory computer readable storage medium for performing image reconstruction using a processor is provided. The non-transitory computer readable storage medium includes instructions to command the processor to acquire emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window. The non-transitory computer readable storage medium also includes instructions to command the processor to perform a preliminary reconstruction of the acquired emission data to create one or more preliminary images of the peak energy window and the scatter energy window and determine a body outline of the person from at least one of the reconstructed preliminary image of the peak energy window or the reconstructed preliminary image of the scatter energy window. The non-transitory computer readable storage medium also includes instructions to command the processor to identify a heart contour of the person from the reconstructed preliminary image of the peak energy window, segment at least the left lung of the person from the reconstructed preliminary image of the scatter energy window using the identified heart contour as a landmark and define an attenuation map based on at least the determined body outline and the segmented left lung. The non-transitory computer readable storage medium further includes instructions to command the processor to reconstruct an image of a region of interest of the person using an iterative joint estimation reconstruction including updating the attenuation map and the image of the peak energy window, wherein the joint estimation reconstruction comprises using data acquired in the plurality of energy windows.

DETAILED DESCRIPTION OF THE INVENTION

Figure 1:
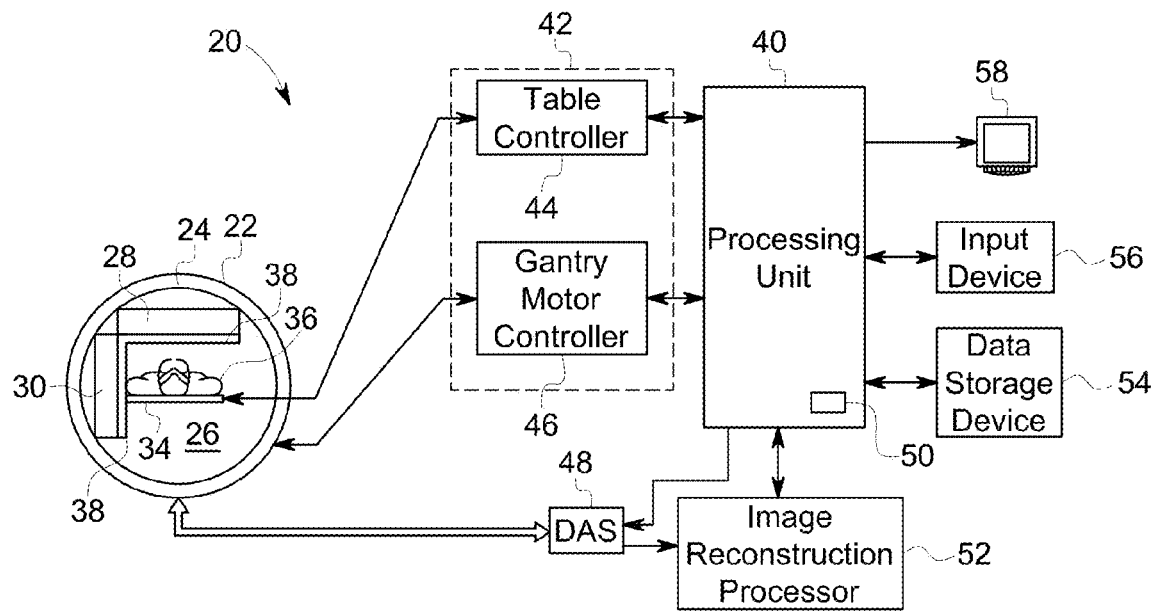
FIG. 1 is a simplified block diagram of an exemplary imaging system constructed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

Described herein are systems and methods to determine and compensate for attenuation within nuclear medicine imaging systems, in particular, single photon emission computer tomography (SPECT) imaging systems. Various embodiments use only emission data acquired by the SPECT system to estimate and compensate for attenuation.

FIG. 1 is a block diagram of an exemplary nuclear medicine imaging system 20 constructed in accordance with various embodiments, which in this embodiment is SPECT imaging system. The system 20 in one embodiment includes an integrated gantry 22 that further includes a rotor 24 oriented about a gantry central bore 26. The rotor 24 is configured to support one or more nuclear medicine (NM) cameras 28 and 30 (two are shown for illustration). In various embodiments the NM cameras 28 and 30 may be, for example, general purpose gamma cameras or non-general purpose gamma cameras, such as focused pinhole gamma camera modules configured for cardiac imaging. The NM cameras 28 and 30 may be formed from different types of suitable material, which may be direct conversion materials or indirect conversion materials, which may be pixelated detectors or cameras. For example, in indirect conversion material, the scintillator, which is typically made of a crystalline material, such as sodium iodide (NaI), converts the received gamma radiation to lower energy light energy (e.g., in an ultraviolet range). In these systems, photomultiplier tubes then receive this light and generate image data corresponding to photons impacting specific discrete picture element (pixel) regions. In direct conversion material, such as cadmium zinc telluride (CZT), the impinging photons are converted directly into electrical signals.

The rotor 24 is further configured to rotate axially about an examination axis including a patient table 34 that may include a bed that is slidingly coupled to a bed support system to support a patient 36, which may be coupled directly to a floor or may be coupled to the gantry 22 through a base coupled to the gantry 22. The bed may include a stretcher slidingly coupled to an upper surface of the bed. The patient table 34 is configured to facilitate ingress and egress of the patient 36 into an examination position that is substantially aligned with the examination axis. During an imaging scan, the patient table 34 may be controlled to move the bed and/or stretcher axially into and out of the bore 26. The operation and control of the imaging system 20 may be performed in any manner known in the art. It should be noted that the various embodiments may be implemented in connection with imaging systems that include rotating gantries or stationary gantries.

A collimator 38 may be provided in combination with the NM cameras 28 and 30. For example, a collimator 38 may be coupled to front detecting faces of each of the NM cameras 28 and 30. The collimators 38 may be any suitable type of collimator known in the art.

The outputs from the NM cameras 28 and 30 are communicated to a processing unit 40, which may be any suitable computer or computing device. As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The processing unit 40 may include an attenuation compensation module 50 to perform attenuation compensation as described in more detail herein. The attenuation compensation module 50 may be implemented in hardware, software, or a combination of hardware and software.

It should be noted that the imaging system 20 may also be a multi-modality imaging system, such as an NM/MR imaging system. During an imaging scan, the patient table 34 may be controlled by a table controller unit 44 that is part of a controller 42. The table controller unit 44 may control the patient table 34 to move the patient table 34 axially into and out of the bore 26. The NM cameras 28 and 30 may be located at multiple positions (e.g., in an L-mode configuration) with respect to the patient 36. It should be noted that although the NM cameras 28 and 30 are configured for movable operation along (or about) the gantry 22, the NM cameras 28 and 30 may be fixed thereto. The controller 42 also includes a gantry motor controller 46 that controls movement of the gantry 22, for example, rotational movement about the patient or movement of the NM cameras 28 and 30, such as pivoting movement or movement towards/away from the patient 36.

Thus, the controller 42 may control the movement and positioning of the patient table 34 with respect to the gamma cameras 28 and 30 and the movement and positioning of the NM cameras 28 and 30 with respect to the patient 36 to position the desired anatomy (e.g., organ(s)) of the patient 36 within the fields of view (FOVs) of the NM cameras 28 and 30, which may be performed prior to acquiring an image of the organ of interest. The table controller 44 and the gantry motor controller 46 each may be automatically commanded by the processing unit 40, manually controlled by an operator, or a combination thereof. The imaging data may be combined and reconstructed into an image as described in more detail below, which may comprise 2D images, a 3D volume or a 3D volume over time (4D).

A Data Acquisition System (DAS) 48 receives analog and/or digital electrical signal data produced by the NM cameras 28 and 30 and decodes the data for subsequent processing as described in more detail herein. An image reconstruction processor 52 receives the data from the DAS 48 and reconstructs an image using any reconstruction process known in the art with attenuation compensation as described herein. A data storage device 54 may be provided to store data from the DAS 48 or reconstructed image data. An input device 56 also may be provided to receive user inputs and a display 58 may be provided to display reconstructed images.

In operation, prior to data collection, a radioisotope, such as a radiopharmaceutical substance (sometimes referred to as a radiotracer), is administered to the patient 36, and may be bound or taken up by particular tissues or organs. Typical radioisotopes include various radioactive forms of elements, although many in SPECT imaging are based upon an isotope of technetium (99Tc) that emits gamma radiation during decay. Various additional substances may be selectively combined with such radioisotopes to target specific areas or tissues of the body.

Gamma radiation emitted by the radioisotope, temporarily present at a location within the patient is detected by the NM cameras 28 and 30. Although the NM cameras 28 and 30 are illustrated in FIG. 1 as planar devices positioned above the patient 36, the NM cameras 28 and 30 may be positioned below the patient 36, both above and below the patient 36, next to the patient 36 and may wrap at least partially around the patient 36.

The imaging system 20 in some embodiments may be coupled to one of more networks to allow for the transfer of system data to and from the imaging system 20, as well as to permit transmission and storage of image data and processed images. For example, a local area networks, wide area networks, wireless networks, and so forth may allow for storage of image data on radiology department information systems or on hospital information systems. Such network connections further allow for transmission of image data to remote post-processing systems, physician offices, and so forth.

The various embodiments described herein may be used, for example, in conjunction with dedicated SPECT systems for imaging particular organs of interest, such as for cardiac imaging and evaluation. Some of these systems are characterized by a limited field of view (FOV) aimed to contain the organ of interest and/or non-parallel collimation. Such systems are sometime referred to as "shift variant" imaging systems. Here, shift variance means that system response to an object (e.g., point source) differs depending on location of the object in the FOV. Among the differences are differences in geometrical shape of system response, system sensitivity, and attenuation path from an emitting object to the system detectors.

Figure 2:
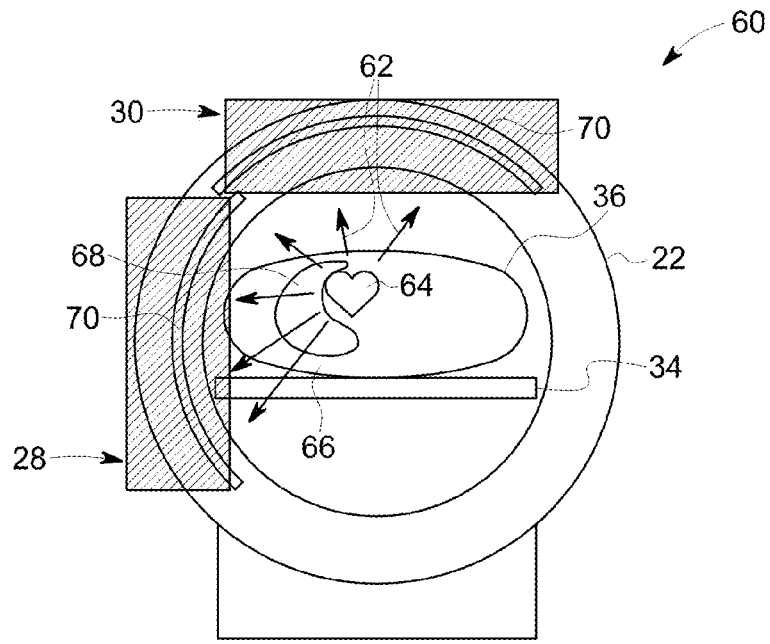
FIG. 2 is a diagram illustrating a detector configuration for the imaging system of FIG. 1 in accordance with one embodiment.
Figure 3:
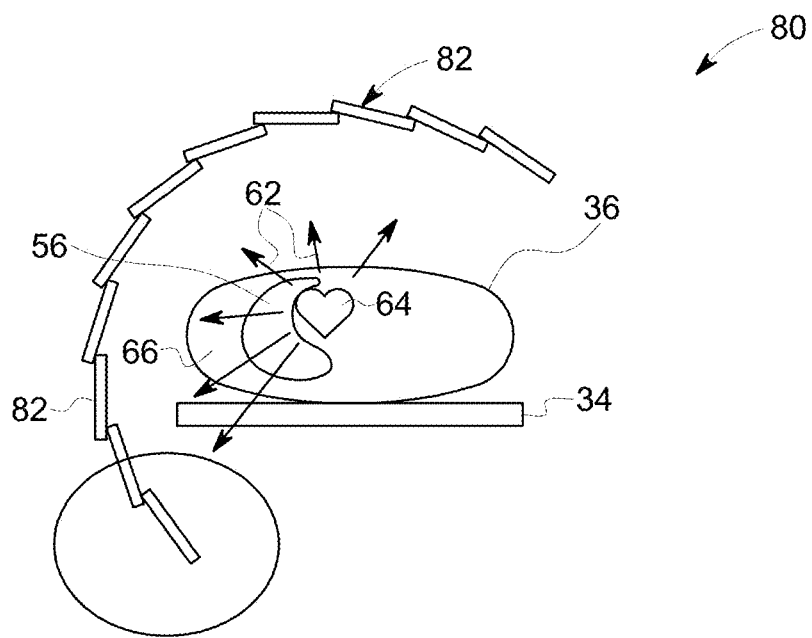
FIG. 3 is a diagram illustrating a detector configuration for the imaging system of FIG. 1 in accordance with another embodiment.

The various embodiments may be used in connection with different SPECT imaging configurations, such as shown in FIGS. 2 and 3. In the embodiment of FIG. 2, an imaging system scanner 60 comprises the gantry 22 that supports a dual head camera (shown in an L-configuration). The camera comprises two camera sections, illustrated as the NM cameras 28 and 30 disposed in the gantry 22 to acquire data over approximately 180 degrees around the patient 36. In the embodiment illustrated, the imaging system scanner 60 is configured for cardiac imaging, and the embodiments described herein allow for characterization and correction of scatter and attenuation of emissions 62 originating at locations in and around the heart 64. In general, such emissions will traverse at least some regions of the heart 64, as well as soft tissues 66 of the body, and particularly the left lung 68. It should be noted that the gamma cameras NM and 30 may be mounted to the gantry 22 with mounting mechanisms 70 that allow for movement in addition to about the patient 36, such as pivoting movement or translation towards or away from the patient 36.

FIG. 3 illustrates another configuration of an imaging scanner 80 allowing that defines a multi-pinhole acquisition system that include a plurality of modules 82, which in this embodiment are pinhole gamma camera modules. The modules 82 are positioned and oriented around the patient volume to collect emissions 62 that traverse similar tissues of the patient 36. It should be noted that in the case of pinhole acquisition systems, the pinholes of the modules 82 may be adjusted such that the pinholes are focused on the volume on interest and may be stationary during image acquisition, for example, the Discovery NM 530 c available from GE Healthcare.

It should also be noted that other types and configurations of cameras may be employed, such as a camera of the type disclosed in U.S. Pat. No. 6,242,743.

Figure 4:
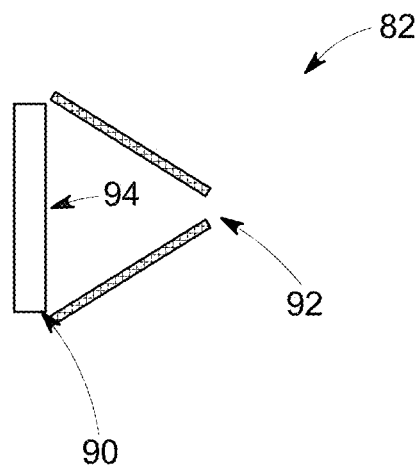
FIG. 4 is a diagram of a detector module formed in accordance with one embodiment.
Figure 5:
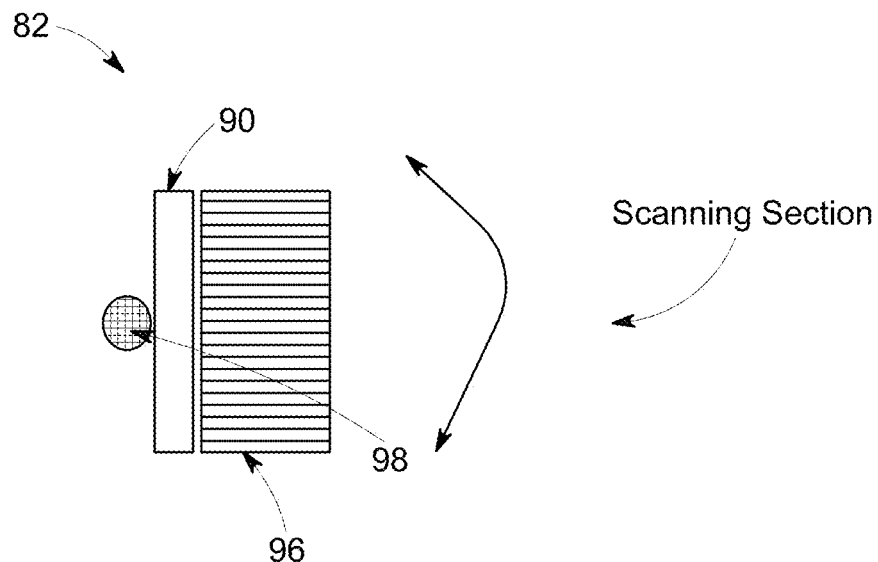
FIG. 5 is a diagram of a detector module formed in accordance with another embodiment.

The modules 82 may take different forms as illustrated in FIGS. 4 and 5. For example, the pinhole configuration as illustrated in FIG. 4 incudes a detector 90 having pinhole collimator 92 in combination therewith, for example, coupled to a detecting face 94 of the detector 90. The module 82 may pivot or rotate.

The module 82 may also include different types of collimation, such as a parallel hole collimator 96 as shown in FIG. 5. However, other types of collimation may be used including diverging and converging types of collimation as known in the art. In the embodiment of FIG. 5, a pivot 98 is provided.

Figure 6:
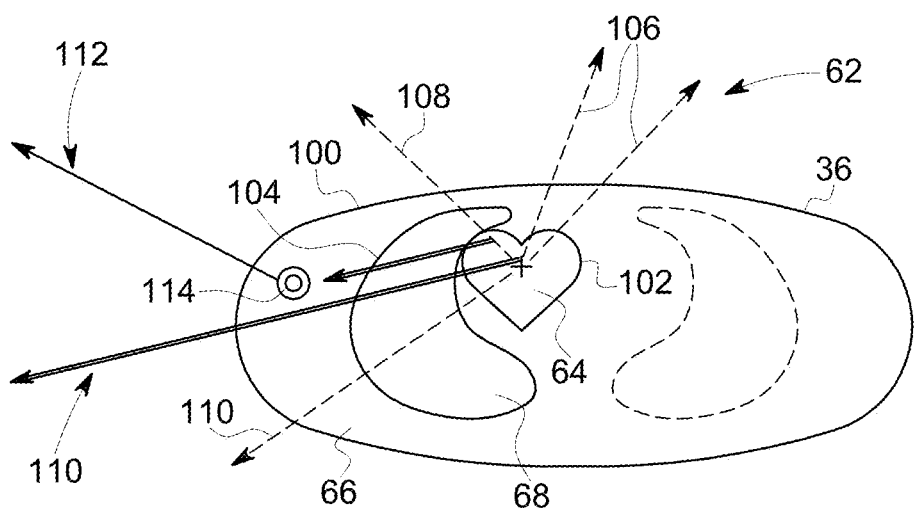
FIG. 6 is a diagram illustrating different emissions.

FIG. 6 illustrates a more detailed illustration of the tissues traversed by the radiation emissions in these scenarios. The body of the patient 36 will extend to a skin-air boundary and have a general contour 100 in the imaging volume from which SPECT data is acquired. Within the body and in the case of cardiac imaging, the heart 64 will have a contour 102 that represents the boundary or transition between the tissues of the heart 64 and those of surrounding anatomies. The lung 68 (which is the left lung) will have a further contour 104 representing the extent and the transition between the lung tissues and those surrounding tissues. During SPECT imaging data acquisition, emissions 62 may radiate in all directions and traverse some or all of these tissues and be scattered and attenuated differently by each. For example, certain lines of radiation 106 may traverse cardiac and soft tissues only, while other lines of radiation 108 may traverse cardiac tissues and lung tissues with little soft tissue therebetween, followed by soft tissue up to the body contour. Still further lines of radiation 110 (direct radiation) may traverse cardiac tissues, soft tissues, and then further traverse the lung and more soft tissue before exiting the body. Some radiation 112 may scatter as well, wherein an electron 114 in the tissue scatters the gamma. The various embodiments use these contours for characterizing the scatter and/or attenuation of the emissions for image data processing and image reconstruction.

Figure 7:
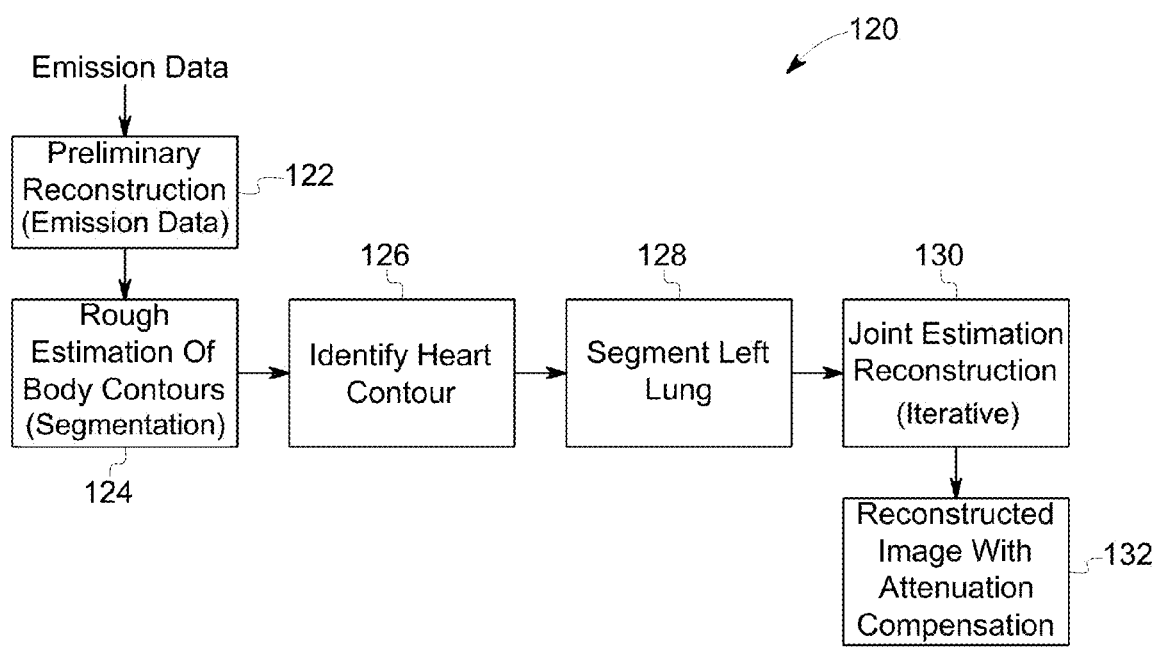
FIG. 7 is a block diagram of a process flow in accordance with various embodiments.
Figure 8:
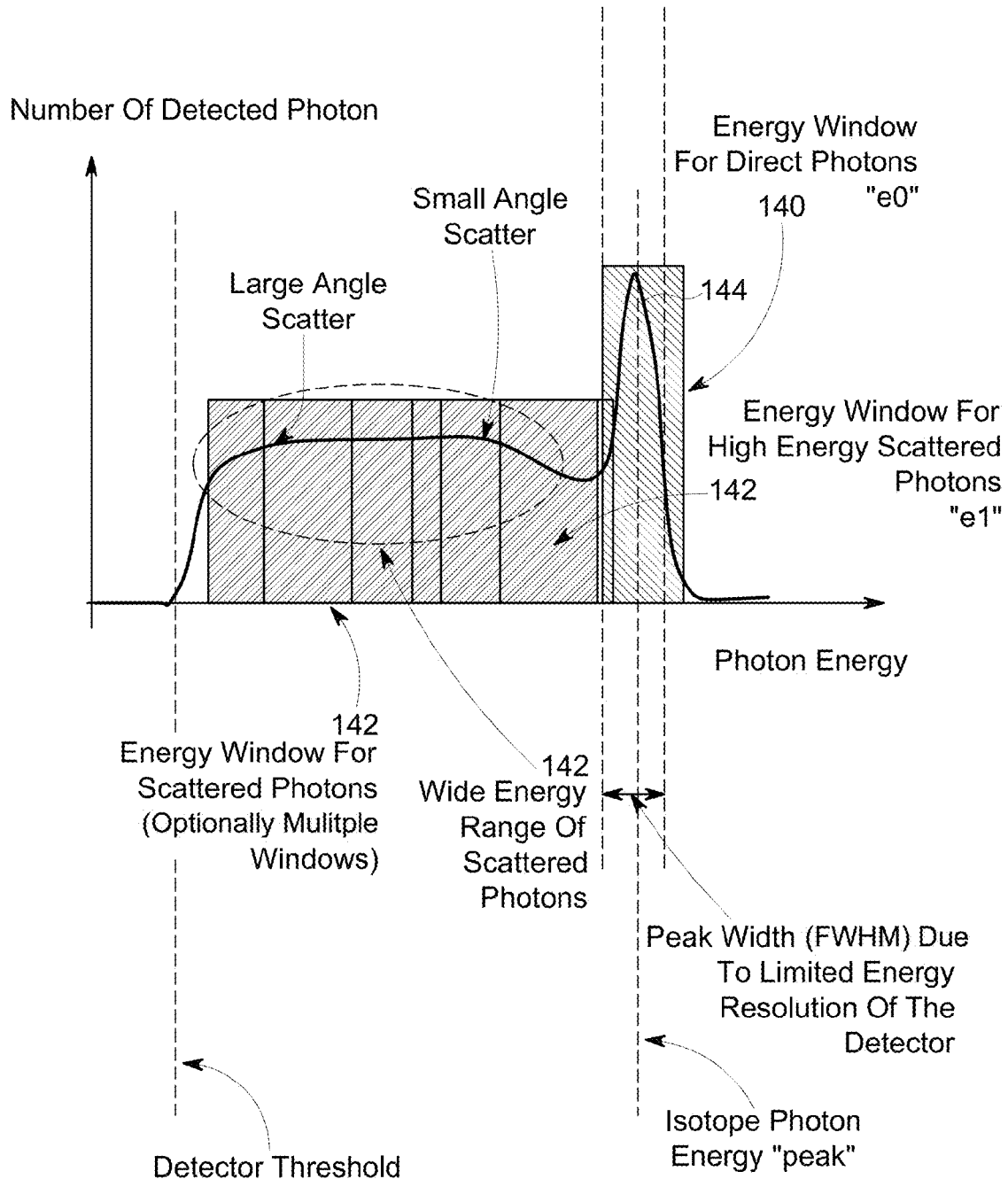
FIG. 8 is a graph illustrating different energy levels in an energy response profile.

Various embodiments provide attenuation correction in SPECT using only emission data. A process flow 120 is shown in FIG. 7 that generally illustrates attenuation compensation performed in some embodiments. A detailed description will then follow. The process flow 120 includes performing a preliminary reconstruction 122 based on acquired emission data. The acquired emission data that is used in the process flow 120 includes a full spectrum of energies in various embodiments as shown in FIG. 8 to create at least preliminary images of the main emission or peak energy window and the one or more scatter windows. Thus, emission data is acquired for a patient at a plurality of energy windows or levels (e.g., list mode data) such that multiple energy windows can be retrospectively defined. For example, a peak energy window, illustrated as the main energy window 140 corresponding to the dominant energy peak in the energy response 144 and one or more scatter energy windows 142 corresponding to lesser or no energy peaks in the energy response 144 are acquired. In various embodiments, the main energy window is generally centered around the peak emission of the isotope and the scatter energy windows are at energy ranges lower than the peak energy window. It should be noted the energy response 144 defines a profile that may identify photons with small angle scatter and large angle scatter. Thus, scatter information, such as in lower energy windows that detect scatter with different scatter angles may be used in various embodiments. It should be noted that scatter with a smaller scatter angle has a smaller deviation and smaller energy loss, while scatter with a larger scatter angle has a larger deviations and larger energy loss.

Referring again to FIG. 7, this preliminary reconstruction 122 is performed without correction for physical effects, namely no attenuation correction. This preliminary reconstruction 122 generally defines a boundary of interest, for example, the outer boundary of the patient. It should be noted that the preliminary reconstruction 122 may be performed using only the main energy window or optionally include scatter data from one or more of the scatter energy windows (to improve outer boundary detection). Thus, a rough estimation 124 of body contours is determined, for example, by segmenting the body outline using a reconstructed preliminary image of the peak energy window and optionally one or more scatter energy windows.

An identification 126 of the heart contour of the patient is then determined using from the reconstructed preliminary image. This identification 126 may be performed using any method known in the art. A segmentation 128 of at least the left lung is then performed, which may include using the identified heart contour to assist the lung segmentation. For example, the boundary between the left ventricle and the lung may be identified and then a seeding and growing process may be used to identify the boundary of the left lung. Thus, the left lung may be segmented from the reconstructed preliminary image of the scatter energy window using the identified heart contour as a landmark.

Binary maps generated from the rough estimation of the body contour and the segmented left lung filled with linear attenuation coefficients are then used as an input to a joint estimation reconstruction 130. The inputs define an initial approximation or guess of the attenuation map, namely a preliminary attenuation map. The joint estimation reconstruction 130 is an iterative process wherein two updates are performed at each iteration. First, an estimate of the attenuation map is used to perform attenuation correction, which is then used to update the emission data. Thus, at each step, the emission estimate is updated based on the attenuation map from the previous iteration step, which is then used to update the attenuation map in the current step. The joint estimation reconstruction 130 is accordingly performed with attenuation and scatter compensation to generate a reconstructed image 132.

Thus, in various embodiments, the body outline is identified using the peak energy window, the scatter energy window or a combination thereof, for example, a summation of the peak energy window and the scatter energy window. The heart contour is identified from the reconstruction "peak". The lung(s) are identified from scatter data, such as using one or more scatter energy windows. Various operations or steps to identify the different landmarks and compensate for attenuation may be performed, for example, as described in more detail below.

Figure 9:
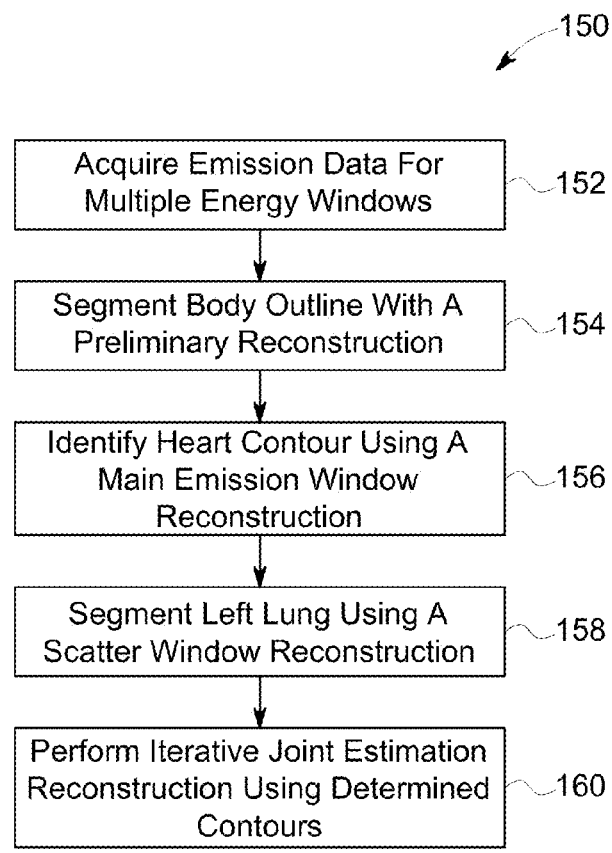
FIG. 9 is a flowchart of a method for attenuation compensation in accordance with various embodiments.

More particularly, various embodiments provide a method 150 as shown in FIG. 9 for attenuation compensation, particularly in SPECT imaging, especially cardiac SPECT imaging. The method 150 includes acquiring emission data for multiple energy windows at 152, which is used to segment a body outline with a preliminary reconstruction at 154. Thus, using emission data for multiple energy windows (peak energy window+scatter energy window(s)), a preliminary reconstruction without attenuation correction is performed. In one embodiment, a main emission or peak energy window reconstruction using any suitable SPECT reconstruction method may be used to determine a rough estimation of the body contour. As described in more detail herein, scatter energy window reconstruction may be used to supplement the main emission or peak energy window reconstruction. Thus, no x-ray CT data is used in the method 150.

Figure 10:
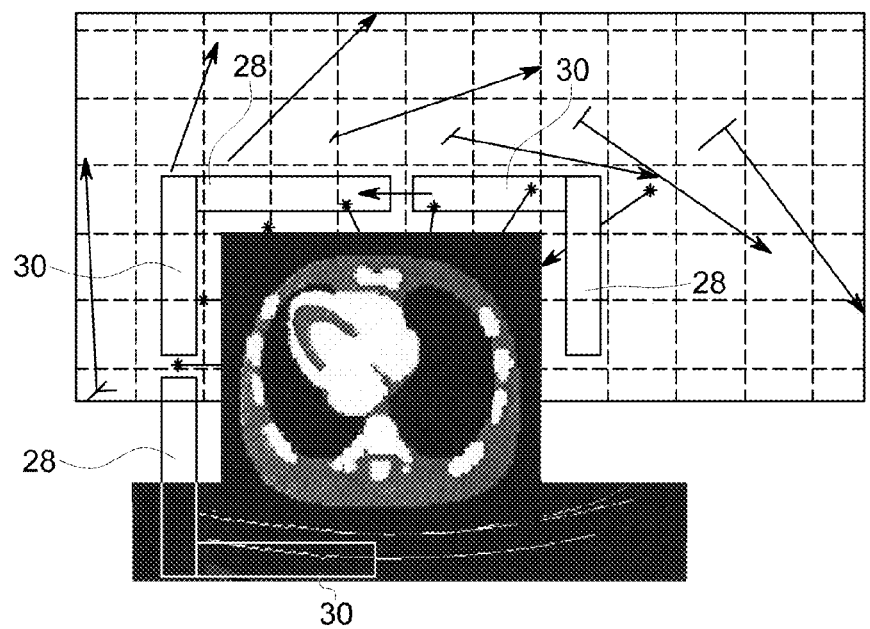
FIG. 10 is a diagram illustrating additional views acquired by detector modules in accordance with various embodiments.

In some embodiments, additional projection views are acquired at 152. For example, additional projection views are acquired from the supine direction to a standard 180 degree acquisition arc as shown in FIG. 10, such as using rotational SPECT. Thus, additional views may be acquired to resolve the body outline by rotating the NM cameras or detectors (e.g., the NM cameras 28 and 30) additional gantry steps, for example, which in one embodiment is a distance about equal to the size of the NM camera or detector. For example, FIG. 10 illustrates three gantry positioned for the NM cameras 28 and 30. It should be noted that the NM cameras 28 and 30 are rotated through a plurality of gantry steps and only three are shown for illustration. As can be seen, locations 1 and 2 are part of the standard 180 degree acquisition while location 3 acquires additional views.

Figure 11:
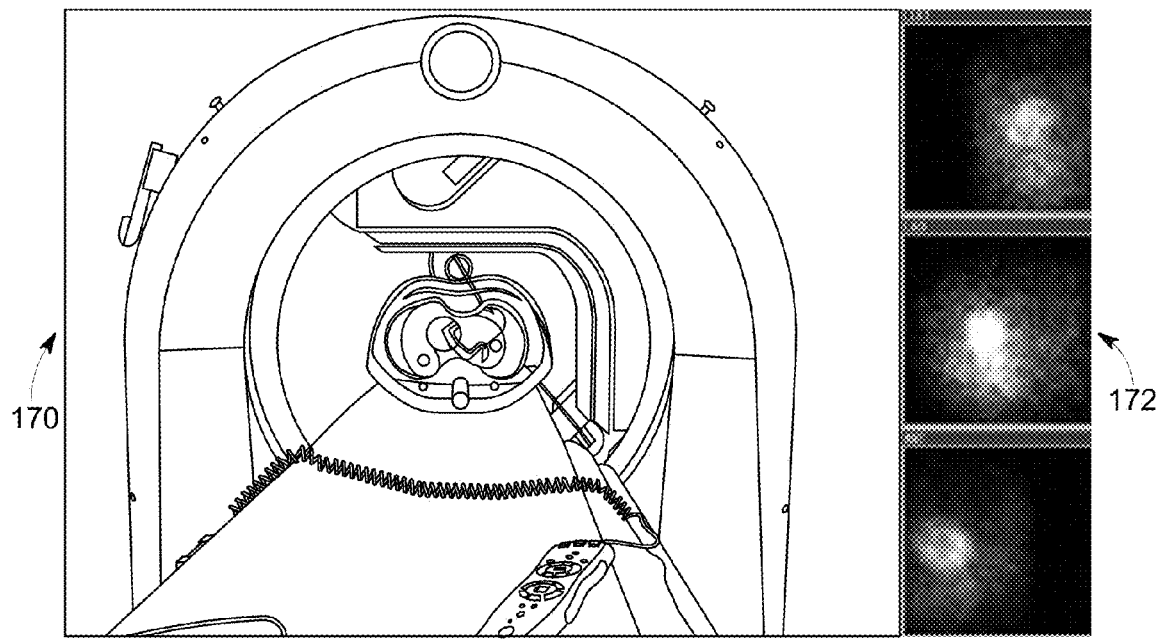
FIG. 11 is a diagram illustrating persistence images used in accordance with various embodiments.

In some embodiments, for example in a focused collimation system 170 (having a focused geometry) as shown in FIG. 11, persistence data 172 may be used. The persistence data 172 is acquired, for example, during positioning of the patient and is not discarded in these embodiments. Thus, this persistence data 172 provides data similar to that of a scout data.

Referring again to FIG. 9, thereafter the heart contour is segmented at 156 from the reconstructed preliminary image of the peak energy window and optionally one or more scatter energy windows. The identification of the heart may be determined using any suitable known heart segmentation method. The heart contour optionally may be used as a landmark to determine an interface between the heart and the left lung to assist in lung segmentation at 158. For example, the heart contour may be enclosed in an ellipsoid (e.g., graphical overlay) with the left lung identified at an interface using a known direction from the left ventricle of the heart.

Thus, at 158, the left lung is segmented using a scatter window reconstruction, namely from the reconstructed preliminary image of the scatter energy window(s). For example, using scatter data, a scatter window reconstruction may be performed using a regular reconstruction, such as a main window reconstruction with straight line projections from the emission to the detector such that geometry changes are ignored. In some embodiments, a special projector for scatter reconstruction may be used such as a model, for example, a Monte-Carlo based method to model the scatter geometry to improve lung contrast. It should be noted that all or a subset of the voxels may be updated at a time.

Thus, a segmentation based determination of the lung may be used to obtain a binary map by using the voxel values and predetermined threshold values, such as to identify tissue. In some embodiments, the segmentation may be assisted by a knowledge set such as an a priori constructed lung model.

Then, an iterative joint estimation reconstruction using data from the determined contours is performed at 160 wherein each iteration includes two updates. In various embodiments, a preliminary attenuation map is defined based on the determined body outline and the segmented left lung. In particular, in each iteration the emission data is reconstructed with an attenuation correction estimate and the attenuation map is updated. For example, a maximum likelihood process may be used for the emission update and a conjugate gradient-like process may be used for the attenuation map update. It should be noted that in some embodiments specifically constructed priors (e.g., adding regularizations), such as joint entropy or other intermediate filters (based on neighbor voxels), or bi-normal distribution may be used to provide smoothness to the resulting images and form the images to develop desired properties.

Thus, various embodiments provide a reconstruction process in two main stages. First, an initial estimate of the attenuation map is created from a series of reconstruction and segmentation steps. Second, this estimate, along with SPECT emission projections, are used as an input (initial approximation) for an iterative joint estimation process, when SPECT data reconstruction with attenuation and, optionally, scatter compensation, and attenuation map estimate are interchangeably updated and refined until a pre-defined criterion is met. It should be noted that the various steps of the method 150 may be achieved in a single step, by reconstructing an optimized scatter window.

Figure 12:
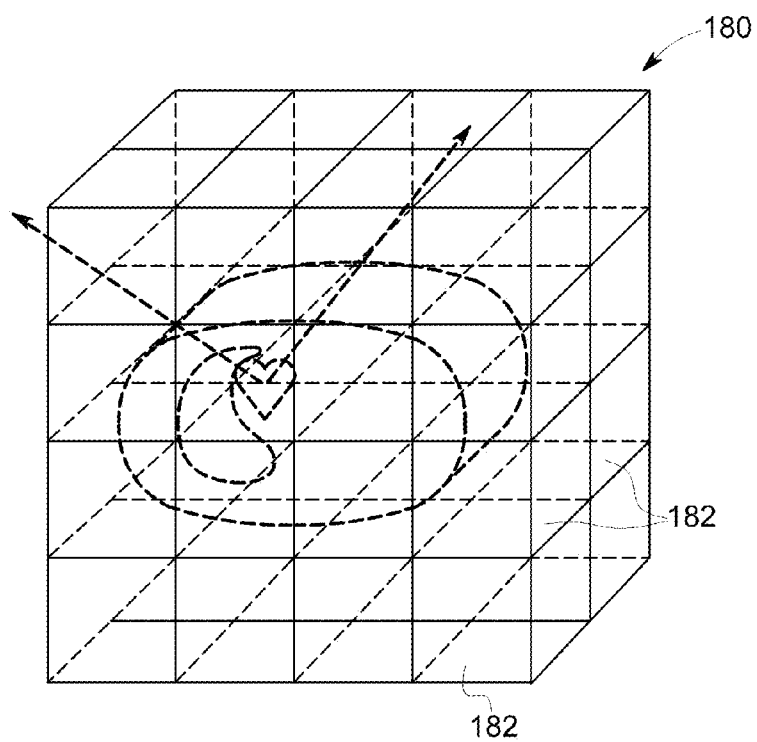
FIG. 12 is a diagram illustrating voxel mapping used in accordance with various embodiments.

Reconstruction with attenuation and scatter compensation may assign a value to the scatter/attenuation for different trajectories through the tissues traversed by each trajectory. For example, FIG. 12 is a diagrammatical illustration of such mapping in the case of cardiac imaging. In this illustration, the mapping 180 is compiled for anatomies of interest and shown disposed in a three-dimensional segment consisting of discrete volume elements or voxels 182. Based upon the density and position of the various tissues, the voxels may indicate more or less scatter/attenuation. The mapping may be determined from the body and tissue contour and volume determinations as described in more detail herein, and used in the reconstruction of images from the acquired SPECT data.

In operation, and for example, the rough estimation of the body contour may be performed in various ways, depending on geometry of acquisition. For conventional rotational SPECT acquisitions, reconstruction of counts in the main emission window, and/or counts detected in the scatter window is used. For alternative geometries, such as characterized by stationary acquisition/limited acquisition arc/small field of view (FOV), additional data, such as scout or persistence data from remote detector positions may be added. In this case, several auxiliary views may be appended to the projection data corresponding to standard acquisition orbit/geometry and reconstructed together, to ensure full visibility of the body outline as described herein. This initial reconstruction will be then segmented into "body" and "outside air" classifications.

Following this body contour estimation phase, and in the case of cardiac imaging, a rough estimation of the left lung volume is performed. This estimation may be based upon "seeding" from the edge of the reconstructed left ventricular surface to provide an additional landmark for lung identification and segmentation. The data resulting from this phase defines an initial estimation of the attenuation maps. The attenuation map is reconstructed on the same voxel grid and volume as the emission data, and from the same data. Thus, the attenuation maps obtained from this process are intrinsically registered to the emission data.

Figure 13:
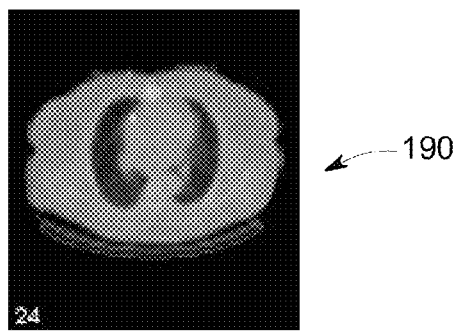
FIG. 13 is a diagram illustrating reconstructed images in accordance with various embodiments.
Figure 13:
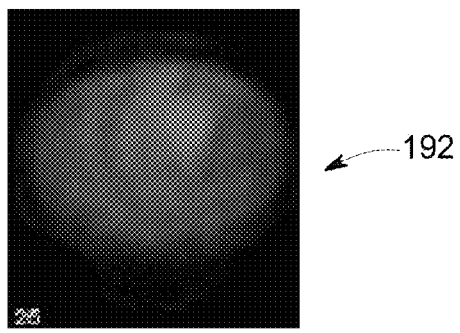
Figure 13:
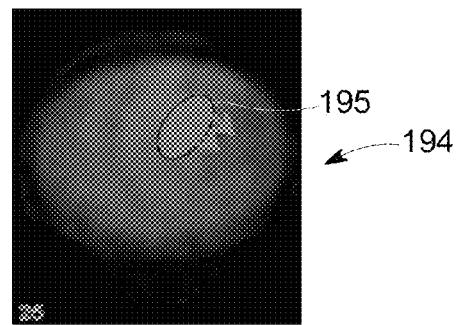
Figure 13:
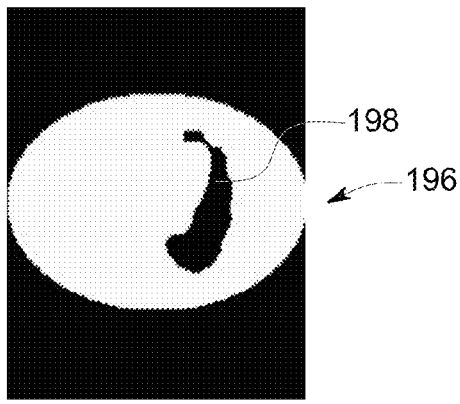

For example, as illustrated in FIG. 13, a preliminary reconstruction of the acquired emission data may be performed to create at least preliminary images 190 and 192 of the peak energy window and scatter energy window, respectively. The heart may be identified as shown in the image 194, including providing an overlay 195 such that the left ventricle contour of the heart is segmented. The arrows in image 194 represent lung search "seeds" to segment the left lung 198 as illustrated in the image 196.

Thus, with the attenuation map determined, image reconstruction with compensation for scatter/attenuation of SPECT emissions may be performed. In various embodiments, the determination of the contours as shown, for example, in FIG. 13, provides the initial estimate of the attenuation map, which will be enhanced further in the process of joint estimation as described herein.

In operation, the second stage of the reconstruction process results in final SPECT images reconstructed with compensation for effects of attenuation and optionally scatter. In accordance with one embodiment, the reconstruction process is iterative, and may be provided as described below. As an initialization step, activity uptake distribution is assumed, in a standard manner, to be uniform in accordance with the relationship:

$$X^{(0)}=M(0)=H'1_p \quad \text{Eq. 1}$$

wherein SPECT emission projections, initial estimate of attenuation map and, optionally, scatter estimate (same volume as the volume of emission reconstruction) are the inputs.

Following initialization, joint estimation is performed. For each iteration of the joint estimation process, two subsequent updates are performed. First, activity concentration estimate x (SPECT reconstruction) is advanced following, for example, a conventional penalized likelihood scheme. In this update, a current estimate of the attenuation map $x^k$ is used. In the second update, the attenuation map estimate is refined using the just obtained activity concentration estimate. The update of the attenuation map, which does not obey Poisson statistics, is not driven by likelihood maximization, but by a general optimization scheme such as a coordinate descent. So, a single iteration of a joint estimation algorithm may be described by the relationships:

$$x^{(k+1)} = \operatorname*{argmin}_x (L(g,x) + \beta P(x, m^{(k)})) \quad \text{Eq. 2}$$

$$m^{(k+1)} = \operatorname*{argmin}_m (F(x^{(k+1)}, m)) \quad \text{Eq. 3}$$

where x represents the activity distribution and in the attenuation map.

From Equation 2, the value of x is updated in accordance with the relationship:

$$x_j^{(k+1)} = \frac{x_j^{(k)}}{\sum_i h_{ij} + \beta \frac{dP(x^{(k)}, m^{(k)})}{dx}} \sum_i h_{ij} \frac{g_i}{\sum_{j'} h_{ij'} x_{j'}^{(k)}} \quad \text{Eq. 4}$$

while a numerical, coordinate descent like framework is applied to advance m. In the process of joint reconstruction, the attenuation map estimate is maintained smooth in various embodiments. Among other ways to ensure this smoothness is a cross-entropy based prior can be utilized, where:

$$P_j(m, \hat{m}) = \sum_{n' \in N_j} w_{j,n'} \left( m_j \ln \frac{m_j}{\hat{m}_{n'}} - m_j + \hat{m}_{n'} \right) \quad \text{Eq. 5}$$

$$\frac{dP(m, \hat{m})}{dx} = \sum_{n' \in N_j} w_{j,n'} \left( \ln \frac{m_j}{\hat{m}_{n'}} - 1 \right)$$

$$\hat{m}_j^{(k)} = \frac{\sum_{n' \in N_j} w_{j,n'} m_j^{(k)}}{\sum_{n' \in N_j} w_{j,n'}}$$

where m is the attenuation map estimate and $\hat{m}$ is some auxiliary image. Under a cross-entropy framework, each voxel of $\hat{m}$ is composed of weighted arithmetic means of its neighboring voxels, imposing smoothness. An edge-preserving constraint may be further implemented.

The values of $m^{(k)}$ are then thresholded in accordance with the relationship single threshold:

$$m_j^{(k+1)} = \begin{cases} m_j^{(k+1)} = \hat{c}; \, m_j^{(k+1)} \geq t^{(k+1)} \\ m_j^{(k+1)} = \check{c}; \, \text{else} \end{cases} \quad \text{Eq. 6}$$

(or using other segmentation techniques described known in the art) into air and soft tissue compartments and filled with linear attenuation coefficients from a look-up table, in accordance with the radiopharmaceutical used in the process of data formation.

Combining the stage of initial independent reconstruction of attenuation map with joint estimation, "cross-talk" is reduced or eliminated. "Cross-talk" appears when emission-specific features (e.g., myocardial uptake) are being propagated into the attenuation map.

Variations and modifications are contemplated. For example, in one embodiment the following process may be provided:

A. Preparation:
1. Data is to be collected in at least two energy windows (E0 and E1).
   E0 is the "peak energy window", defined as "peak energy+/−dE wherein dE is usually a few percent;
   E1 is energy window within the scatter energy range wherein the energy range of the "scatter energy window" is below the "peak energy window", and in various embodiments is wider than the "peak energy window";
   Optionally more scatter energy windows are defined such as E2 (or more), that is, the "scatter energy window" is divided to two or more sub-windows, which in some embodiments are non-overlapping, contiguous sub-windows. 2. Defining the system response function—a function that allows estimating the data provided that the object is known. The system response depends on the collimator, the detector, etc.

B. Data Acquisition:
Collecting emission data "e(P,E)", the number of photons collected at detector position "P" at energy window "E". Here, "E" are the energy windows (E=0, 1, 2, . . . ) and "P" is the general designation of the detector position.
1. In a multi-pinhole camera P={x,y,p} wherein x, y are the pixel indexes and p is the pinhole index.
2. In a rotating SPECT camera, P={x,y,p} wherein x, y are the pixel indexes and p is the projection index (the gantry angle "f").
3. In a camera with a plurality of rotating, collimated heads (such as in FIG. 5), P={x,y,p, f} wherein x, y are the pixel indexes and p is the head index, and f is the angle of head p. Optionally, f is defined by f={fx,fy} if the heads can rotate in 2D.

It should be noted that the dimension of the dataset is x*y*p*e (e=2 for two energy windows: "e0=peak"; and "e1=scatter", optionally e>2 if the scatter window is subdivided). It also should be noted that the solution is of the same (or lower) dimensionality.

C. Assumption and Definitions
It should be noted that a single isotope having a single emission peak is assumed, (e.g. Tc having a peak at 140 keV), but extension to multi-peak isotope or multi-isotope may be provided.
1. The Object (patient)
The object O(X)={S,D}(X) is defined by both its:
"Source Concentration" S(x,y,z) S(X); (S is in "Curie per cc", x,y,z=X are the voxel index in 3D). Typically, the dimensionality of x=y=z=64 or 128, the source concentration must be a non-negative number and "body density" D(x,y,z)=D(X); (D in grams per cc). It should be noted that D(x,y,z) may be translated to "Absorption & Compton scattering coefficients" by the energy dependent nuclear parameters cross section parameters. Typically, a linear transformation is applied, but non-linear transformations (that take into account bone chemical composition) are also known.

Tissue Segmentation.

To reduce the complexity of computation, the following algorithm may be applied to D(X):

1. Air—For D~0 (or below a threshold)—the tissue is assumed to be "Air". Specifically if it can be located as being outside the patient boundaries. D is then set to D=0
2. Lungs—For D between "minimal lung density" and "Maximum lung density"—The tissue a mixture of air and soft tissue, with the required mixture percentage. Specifically if tissue can be located as being inside the patient lungs boundaries. D is left as a variable,
3. Soft tissue—For D between "maximal lung density" and "minimal spongy bone density"—The tissue is assumed soft tissue. D is set to the soft tissue average value
4. Spongy Bone—For D between "minimal spongy bone density" and "maximal spongy bone density"—The tissue a mixture of soft tissue and bone, with the required mixture percentage. D is left as a variable and the chemical composition is assumed to be the appropriate mixture of hard bone and soft tissue having density D.
5. Hard bone—For D between "minimal hard bone density" and "maximal hard bone density"—The tissue a hard bone. D is set to density and hard bone.
6. Metal—For D above "maximal hard bone density"—The tissue an implant or foreign object—operator intervention is required.

This process is called "segmentation of the patient tissue" (the segments are: air, lungs, soft tissue, spongy bones, and hard bone. However, in some cases, only air, lungs, and soft tissue are considered and bones are ignored and replaced with soft tissue or with "dense soft tissue having same artificially high density).

Segmentation reduces the computation as most of the volume comprises air or soft tissue.

The simple (linear) transformation from D to absorption and scattering coefficients is:

Absorption $A(X,E)=a(E)*D(X)$; wherein "a" is the average absorption coefficient of tissue for energy E (ignoring minor variation due to tissue types)

Compton scattering $C(X,E,E')=c(E,E')*D(X)$ wherein $c(E,E')$ is the average is the average Compton scattering coefficient of tissue from energy E to energy E' (which also define the scattering angle, so in fact we could define $C(X,E,t)=c(E,t)*D(X)$ wherein "t" is the scattering angle)

Also note that the total attenuation $U(X,E)$ is:

$U(X,E)=A(X,E)$ Sum$[\{E'\}, C(X,E,E')]$ wherein Sum$[\{E'\}, C(X,E,E')]$ is the summation for all E' (or angles t) of $C(X,E,E')$.

2. The acquired data set

The emission data set is defined as $e(P,E)=\{e0,e1,e2\ldots\}(P)$ wherein:

e0 is the number of photons detected having energy e0, etc. (generally, e0 will be the un-scattered emission energy, while e1,e2 ... eN are the Compton scattered energies e1,e2 ... eN<e0.

P is generalized pixel number.

In a "stationary pinhole camera" P=(p,x,y) wherein p is the pinhole number, x,y, are the pixel indexes associated with the pixel.

In a SPECT (rotating) camera, P=(f,x,y) wherein f is the projection angle

In "Spectrum Dynamic" camera, P=(h,f,x,y) wherein h is the head number, f is the head' angle.

Forward Projection—Estimation of "Peak" Data e0'(P) from S(X) and D(X)

Whatever the system is, P indicates the camera configuration. Each P, is associated with a matrix element in the "response function Matrix" M(P,X) which associate (gives the response, or the sensitivity of the detector) a detected photon at generalized pixel P with a radioactive source in location (voxel) X in the body.

In a general sense, M(P,X) is the response function, define as the probability of detecting a photon which was randomly emitted from location X at generalized datum pixel P given the camera geometry (including for example collimation, detector sensitivity, etc. This may make M(P,X)=>M(P,X.E) for example given energy dependence of septa penetration and/or detector response), but excluding patient attenuation.

With absence of attenuation (D(X)=0), a source S(X) will (statistically speaking—it is estimated to most likely to) produce an acquired data $e(P,E)=\{e0,e1,e2\ldots\}(P)=\{M(P,X)*S(X), 0, 0, \ldots\}$ or $e0(P)=M(P,X)*S(X)$. Note that M is very sparse (most of M elements are zero)

However, in presence of a real patient, the equation is modified by attenuating each photon by the integrated (summed) total attenuation U(X, e0) (as derived from D(X) along the traveling line from the corresponding X to P.

Forward Scatter Estimation—Estimation of "Scattered" Data e1'(P) from S(X) and D(X) (for Multi Scatter Windows—Also e2'(P), Etc)

There are several known methods disclosed in the art to calculate e1'(P) when S'(X) and D'(X) are assumed known.

For example, "Monte Carlo simulations" may be used. Generally, these are computational intensive (takes long time). Thus, according to one embodiment, estimation of scattered data by "accelerated Monte Carlo" may comprise the following simplifications:

1. Define only one scatter window e1(P) at high energy range of the scatter spectrum.
2. As a consequence:
   A. Only scattering into small angles ("alpha max" which produces less than the max energy loss) needs to be computed, and
   B. second order scattering can be ignored.
   C. Attenuation coefficient of the scattered photon may be taken as a single average value U(X,e1'), where e1' is the average energy of the photons in window e1.

The "Monte Carlo" simulation is accelerated if the following steps are ignored:

1. For emitted photons:
   A. ignore propagation direction in which there are no possible valid scattering from them to the detector (taking into account the limited "alpha max" and the collimator acceptance).
   B. If the path reaches pure air (out of the patient)—terminate the photon.
   C. Optionally ignore locations where S(X) us below a threshold value.

2. Compute only the first scattering process (taking into account D(X)): In this compute only:
   A. Scattering a less than "alpha max"; and
   B. Only into valid acceptance directions of the collimator(s)
3. Adjust for absorption by (taking into account D'(X)):
   A. U(X, e0) for the path from X0 to X1 (wherein X0 is the origin of the photon and X1 is the location of the scatter event); and
   B. U(X, e1') for the path from X1 to P (wherein X1 is the location of the scatter event, and P is the detection pixel); and Thus, various embodiments find an accurate estimation S'(X) which is as close as possible to the true source S(X) distribution.

For finding S'(X) an accurate estimation D'(X) which is as close as possible to the true density D(X) is determined. D'(X) is used for attenuation correction of the emission image. D'(X) may be useful for the operator for orienting S'(X) within the patient's body; and for ability to register the image with anatomical images such as CT or MRI.

In some embodiments, a combined reconstruction algorithm may be provided that includes:
1. measure data {e0(P), e1(P)}
2. start with initial guess {S'(X), D'(X)}
3. estimation of {e0'(P), e1'(P)} by forward projection of guess {S'(X), D'(X)}
4. compare estimation {e0'(P), e1'(P)} to measured data {e0(P), e1(P)}
5. update guess {S'(X), D'(X)} in view of #4
6. decision if to repeat steps #3 to #5, if not:
7. post processing and display the last updated guess {S'(X), D'(X)}. (post processing may comprise filtering and image analysis as known in the art)
8. stop An operational alternative includes: Steps #3, #4, and #5 can be repeated a few times for S'(X) and e0'(P) only (which is more important, and less time consuming), then performing the steps for D'(X) and e1'(P). However, it should be noted that the combined problem is harder in several aspects:
1. The object is more complex: O(X)={S,D} (X)—there are two unknown to find per "X"
2. The data set e(P) is more complex e(P)={e0, e1}(P)—there are two measured value per "P"
3. Estimation of data has two parts:
   a. Estimation of e0(P) as known in the art; and
   b. Estimation of e1(P) as disclosed in the accelerated Monte Carlo (above).
4. Updating the guess has two parts:
   a. Updating the source S'(X) as known in the art (keeping for example the following limitations: 1. positivity of S(X), and 2. S(X)=0 outside the patient boundary); and
   b. Updating the density D'(X) (keeping for example the following limitations: 1. positivity of D'(X), 2. D'(X)=0 outside the patient boundary, 3. segmentation of D'(X) as disclosed above).
   According to one embodiment, updating the guess D'(X) may comprise the following:
   1. Subtract the estimated scattered data from measured scattered data to obtain error function:

ERR(P)=e1(P)−e1'(P).

2. Reconstruct ERR(P) to produce a suggested change to guessed density deltaD'(X). Reconstruction may be done by methods known in the art. The reconstructed deltaD'(X) may be positive or negative, but it may limited by the following requirements:
      Positivity of D'(X)—that is deltaD'(X) may not be larger than D'(X)
      Limited range of D(X)—that is deltaD'(X)+D'(X) must not be larger than "density of hard bone".
      deltaD'(X)=0 outside the patient boundary
   3. Update the guess of the density to be D'(X)=>D'(X)+deltaD'(X)

Decision to stop (#6) may depend on the number of iterations and/or requiring a minimal match between both e0' and e0 AND e1' and e1

Initial Approximation

According to various embodiments:
1. Body boundary is calculated by reconstruction of e0(P)+e1(P) (without attenuation correction), and defining the outer perimeter outside which the reconstructed value is less than a threshold value. Optionally a one or two "outward voxels expansion" is performed to ensure that body parts are all included within the boundary.
3. Initial guess for D'(X) may be taken as one of:
   A. Defining all the volume within the body boundary (calculated in #1) as "soft tissue"
   B. Defining all the volume within the body boundary (calculated in #1) as "soft tissue", then introducing "average lungs" by "morphing" lungs from "average patient atlas"
   C. Calculating D'(X) by reconstruction of e1(P) without attenuation correction, but using the segmentation limitation (disclosed above) and body boundary.
4. Initial guess for S'(X) is calculated by reconstruction of e0(P) using methods of the art, using optionally:
   A. Attenuation correction using D'(X) from above; and
   B. Body boundaries from above.

A technical effect of various embodiments described herein include attenuation compensation using only emission data.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for image reconstruction, the method comprising:
    acquiring emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window;
    performing a preliminary reconstruction of the acquired emission data to create one or more preliminary images of the peak energy window and the scatter energy window;
    determining a body outline of the person from at least one of the reconstructed preliminary image of the peak energy window or the reconstructed preliminary image of the scatter energy window;
    identifying a heart contour of the person from the reconstructed preliminary image of the peak energy window;
    segmenting at least the left lung of the person from the reconstructed preliminary image of the scatter energy window using the identified heart contour as a landmark;
    defining an attenuation map based on at least the determined body outline and the segmented left lung; and
    reconstructing an image of a region of interest of the person using an iterative joint estimation reconstruction including updating the attenuation map and the image of the peak energy window, wherein the joint estimation reconstruction comprises using data acquired in the plurality of energy windows.

2. The method of claim 1, wherein the preliminary reconstruction is performed without using x-ray computed tomography (CT) data.

3. The method of claim 1, wherein acquiring the emission data comprises performing a 180 degree single-photon emission computed tomography (SPECT) acquisition scan arc.

4. The method of claim 3, further comprising acquiring additional views from a supine direction.

5. The method of claim 3, further comprising using persistence data in the peak energy window reconstruction to segment the body outline.

6. The method of claim 1, wherein segmenting the left lung comprises scatter window reconstruction using a Monte-Carlo based projection estimation method.

7. The method of claim 1, wherein segmenting the left lung comprises using an a priori lung model.

8. The method of claim 1, wherein the updating during the iterative joint estimation reconstruction comprises for each iteration using a penalized likelihood maximization scheme to determine an updated activity distribution estimate for the peak energy window.

9. The method of claim 8, wherein the updating during the iterative joint estimation reconstruction comprises updating the attenuation map using the updated activity distribution estimate.

10. The method of claim 8, wherein the updating during the iterative joint estimation reconstruction comprises updating the attenuation map using a conjugate gradient method.

11. The method of claim 1, wherein the updating during the iterative joint estimation reconstruction comprises using a constructed prior including one of a joint entropy prior or a bi-normal distribution prior.

12. The method of claim 1, further comprising reconstructing the attenuation map on the same voxel grid and volume as the emission data.

13. The method of claim 1, wherein acquiring the emission data comprises acquiring the data in at least a peak energy window and a plurality of scatter energy windows.

14. The method of claim 13, further comprising segmenting tissue.

15. The method of claim 1, further comprising performing a forward projection to determine scatter data using the same emission projections as the emission data.

16. A nuclear medicine (NM) imaging system comprising:
a gantry;
a plurality of nuclear medicine (NM) cameras coupled to the gantry and configured to acquire emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window; and
an image reconstruction module configured to (i) perform a preliminary reconstruction of the acquired emission data to create one or more preliminary images of the peak energy window and the scatter energy window, (ii) determine a body outline of the person from at least one of the reconstructed preliminary image of the peak energy window or the reconstructed preliminary image of the scatter energy window, (iii) identify a heart contour of the person from the reconstructed preliminary image of the peak energy window, (iv) segment at least the left lung of the person from the reconstructed preliminary image of the scatter energy window using the identified heart contour as a landmark, (v) define an attenuation map based on at least the determined body outline and the segmented left lung and (vi) reconstruct an image of a region of interest of the person using an iterative joint estimation reconstruction including updating the attenuation map and the image of the peak energy window, wherein the joint estimation reconstruction comprises using data acquired in the plurality of energy windows.

17. The NM imaging system of claim 16, wherein the image reconstruction module is configured to perform the preliminary reconstruction without using x-ray computed tomography (CT) data.

18. The NM imaging system of claim 16, wherein the plurality of NM cameras are configured to rotate about the person to acquire the emission data from a 180 degree single-photon emission computed tomography (SPECT) acquisition scan arc.

19. The NM imaging system of claim 16, wherein the plurality of NM cameras are configured to acquire additional views of the person from a supine direction.

20. The NM imaging system of claim 16, wherein the image reconstruction module is configured to use persistence data acquired by the plurality of NM cameras in the peak energy window reconstruction to segment the body outline.

21. The NM imaging system of claim 16, wherein the plurality of NM cameras comprises focused detector modules in a fixed orientation on the gantry.

22. The NM imaging system of claim 16, wherein the image reconstruction module is configured to segment the left lung by at least one of (i) modeling scatter using a Monte-Carlo based estimation method or (ii) using an a priori lung model.

23. The NM imaging system of claim 16, wherein the image reconstruction module is configured to update at each iteration of the iterative joint estimation reconstruction the attenuation map using at least one of (i) an updated activity distribution estimate determined from the iterative joint estimation reconstruction wherein for each iteration a penalized likelihood maximization scheme is used to determine the updated activity distribution estimate for the peak energy window or (ii) a conjugate gradient method.

24. The NM imaging system of claim 16, wherein the image reconstruction module is configured to use during the iterative joint estimation reconstruction a constructed prior including one of a joint entropy prior or a bi-normal distribution prior.

25. The NM imaging system of claim 16, wherein the plurality of NM cameras are configured to acquire the emission data in at least a peak energy window and a plurality of scatter energy windows.

26. A non-transitory computer readable storage medium for performing image reconstruction using a processor, the non-transitory computer readable storage medium including instructions to command the processor to:
acquire emission data at a plurality of energy windows for a person having administered thereto a radiopharmaceutical comprising at least one radioactive isotope, wherein the energy windows comprise (i) at least a peak energy window centered around a peak emission of the isotope and (ii) at least one scatter energy window at an energy range lower than the peak energy window;
perform a preliminary reconstruction of the acquired emission data to create one or more preliminary images of the peak energy window and the scatter energy window;
determine a body outline of the person from at least one of the reconstructed preliminary image of the peak energy window or the reconstructed preliminary image of the scatter energy window;
identify a heart contour of the person from the reconstructed preliminary image of the peak energy window;
segment at least the left lung of the person from the reconstructed preliminary image of the scatter energy window using the identified heart contour as a landmark;
define an attenuation map based on at least the determined body outline and the segmented left lung; and
reconstruct an image of a region of interest of the person using an iterative joint estimation reconstruction including updating the attenuation map and the image of the peak energy window, wherein the joint estimation reconstruction comprises using data acquired in the plurality of energy windows.

* * * * *